United States Patent
Bellam et al.

(10) Patent No.: US 8,731,969 B1
(45) Date of Patent: May 20, 2014

(54) INTERACTIVE SYSTEM FOR PATIENT ACCESS TO ELECTRONIC MEDICAL RECORDS

(71) Applicant: Epic Systems Corporation, Verona, WI (US)

(72) Inventors: Sashidhar Bellam, Madison, WI (US); Sumit Rana, Verona, WI (US); Davin Sannes, Mount Horeb, WI (US); Bhavik Shah, Aurora, IL (US); Sapan Anand, Jersey City, NJ (US); Christine Marie Benson, Sandy, UT (US); Matthew Sidney, Madison, WI (US)

(73) Assignee: Epic Systems Corporation, Verona, WI (US)

( * ) Notice: Subject to any disclaimer, the term of this patent is extended or adjusted under 35 U.S.C. 154(b) by 0 days.

(21) Appl. No.: 13/867,279

(22) Filed: Apr. 22, 2013

Related U.S. Application Data

(63) Continuation of application No. 10/842,080, filed on May 10, 2004, now Pat. No. 8,428,968.

(51) Int. Cl.
*A61B 5/00* (2006.01)
*G06F 19/00* (2011.01)

(52) U.S. Cl.
USPC .................................................. 705/3

(58) Field of Classification Search
USPC .............................................. 705/2, 3
See application file for complete search history.

(56) References Cited

U.S. PATENT DOCUMENTS

| | | | |
|---|---|---|---|
| 2001/0039503 A1* | 11/2001 | Chan et al. | 705/2 |
| 2003/0153819 A1* | 8/2003 | Iliff | 600/300 |
| 2004/0030704 A1* | 2/2004 | Stefanchik et al. | 707/100 |
| 2004/0078236 A1* | 4/2004 | Stoodley et al. | 705/2 |
| 2005/0055242 A1* | 3/2005 | Bello et al. | 705/2 |

* cited by examiner

*Primary Examiner* — John Pauls
*Assistant Examiner* — Trang Nguyen
(74) *Attorney, Agent, or Firm* — Boyle Fredrickson, S.C.

(57) ABSTRACT

A programmable rules-based interface between a patient and an electronic medical record EMR allows controlled patient access to the EMR allowing increased patient participation in the healthcare process.

20 Claims, 2 Drawing Sheets

US 8,731,969 B1

INTERACTIVE SYSTEM FOR PATIENT ACCESS TO ELECTRONIC MEDICAL RECORDS

CROSS-REFERENCE TO RELATED APPLICATION

This application is a continuation of U.S. patent application Ser. No. 10/842,080, entitled "Interactive System for Patient Access to Electronic Medical Records," filed May 10, 2004, the disclosure of which is hereby expressly incorporated by reference.

FIELD OF THE INVENTION

The present invention relates to electronic medical record (EMR) systems and in particular to an EMR system allowing access to and entry of data by a patient.

BACKGROUND OF THE INVENTION

Enlisting patients as active participants in their own healthcare can increase patient satisfaction and the quality of the healthcare experience while decreasing the cost of providing that care.

A number of healthcare organizations and other enterprises have used the Internet to provide basic information to patients allow the scheduling of appointments, and to provide interactive healthcare calculators and the like which allow patient-sourced data to be input and certain information to be returned. While these services allow more patient involvement in the healthcare process, the information provided by and to the patient is held separate from the centralized electronic medical record (EMR) that provides a cohesive repository of medical information for doctors and other healthcare providers.

This isolation of the patient from the EMR is done for good reason. Preventing patients from entering data into the EMR preserves the validity of the EMR data so that it may be relied upon by other healthcare professionals. Patients often unfamiliar with the data they are collecting are likely more prone to make significant mistakes in that data entry than a healthcare provider.

Further, the data in the EMR, intended for healthcare professionals, is often unintelligible by patients and some aspects of the data could be confusing or unnecessarily alarming to a layperson. The act of a healthcare professional entering medical information is often the juncture at which the data is reviewed or considered by the healthcare professional in detecting possible problems. Entry of data by patients eliminates this important juncture. Finally, issues of medical privacy make it desirable to limit to the extent possible, broad access to the electronic medical record. Medical privacy laws prohibit medical data from being made available to the parties not authorized by the patient and some medical data from being made available to the patient except in the presence of a qualified healthcare professional.

This need to separate the patient from the integrating features of the EMR limits the ability to which the patient may significantly contribute to his or her healthcare.

SUMMARY OF THE INVENTION

The present invention provides practical access by a patient to the information in his or her EMR, significantly improving communication between a patient and their healthcare organization. Critical to the invention is a set of administrator programmable rules based on data from the EMR that control this access, limiting access to certain data, interpreting the data for the patient as necessary, and marking data from the patient so as to indicate its accuracy and level of review. Access to the EMR data allows improved information to be provided to the patient by processing patient-sourced data according to information stored in the EMR to provide data range checking and trend analyses. The invention communicates with a healthcare provider so that patient-sourced data can be reviewed and health issues brought to the attention of the healthcare provider much as if the healthcare provider entered the data his or herself. This invention may allow direct patient/physician communication using secured messaging.

Specifically, the invention pertains to a computer-implemented electronic medical record (EMR) access control system configured to implement an access program stored on a computer-readable medium. The system includes a computer, which when controlled by the access control program, is configured to receive patient-sourced medical data about a patient from the patient at a computer system, generate a trend analysis based on previously received patient-sourced medical data, generate a patient specific data range based on data in a computer-implemented electronic medical record system of a healthcare provider that does not include patient-sourced medical data, compare the received patient-sourced medical data to the trend analysis and the patient specific data range; and incorporate the received patient-sourced medical data based on the comparison into a patient-sourced medical data of the computer-implemented electronic medical record system, tagging the received data as patient-sourced medical data to generate tagged patient sourced medical data store on the computer system. Such a system is provided wherein the access program is configured to block access to the computer-implemented electronic medical record system by the patient.

It is thus a feature of at least one embodiment of the invention to provide such a system where comparing the received patient-sourced medical data to the trend analysis and the patient specific data range includes testing the data for entry errors based on knowledge about the patient held in the electronic medical record of the healthcare provider. Further where the patient is notified of the entry errors to permit re-entry of the patient-sourced medical data.

It is thus a feature of at least one embodiment of the invention to provide such a system further including providing output to the patient indicating a medical issue based on the comparison, where the computer provides the patient with prepared background information about the medical issue and/or where the computer provides the patient with clinical options for assisting in correcting the medical issue. The system may alternatively be provided such that the patient is prompted to seek healthcare support.

It is thus a feature of at least one embodiment of the invention to provide a system where a healthcare professional is notified of abnormal conditions indicated by the patient-sourced data to permit review of the patient-sourced data and further where the healthcare professional is notified by a secure electronic message.

It is thus a feature of at least one embodiment of the invention to provide such a system where the patient-sourced data is selected from the group consisting of: patient's weight, blood glucose, blood pressure, pain level, previous health conditions, heart rate, temperature, last menstrual period, and dialysis status, where the patient-sourced data from the patient is authenticated by a patient specific token, where the electronic medical record of the healthcare provider holds medical data provided by different healthcare professionals for multiple patients, where the access control program includes a web server and the patient-sourced data is received over the Internet from a web browser, and/or where patient-sourced data is selected from a source consisting of: machine-generated data from home healthcare appliances and patient-collected data manually input by a patient.

Other features and advantages of the invention will become apparent to those skilled in the art upon review of the following detailed description, claims and drawings in which like numerals are used to designate like features.

Figure 1:
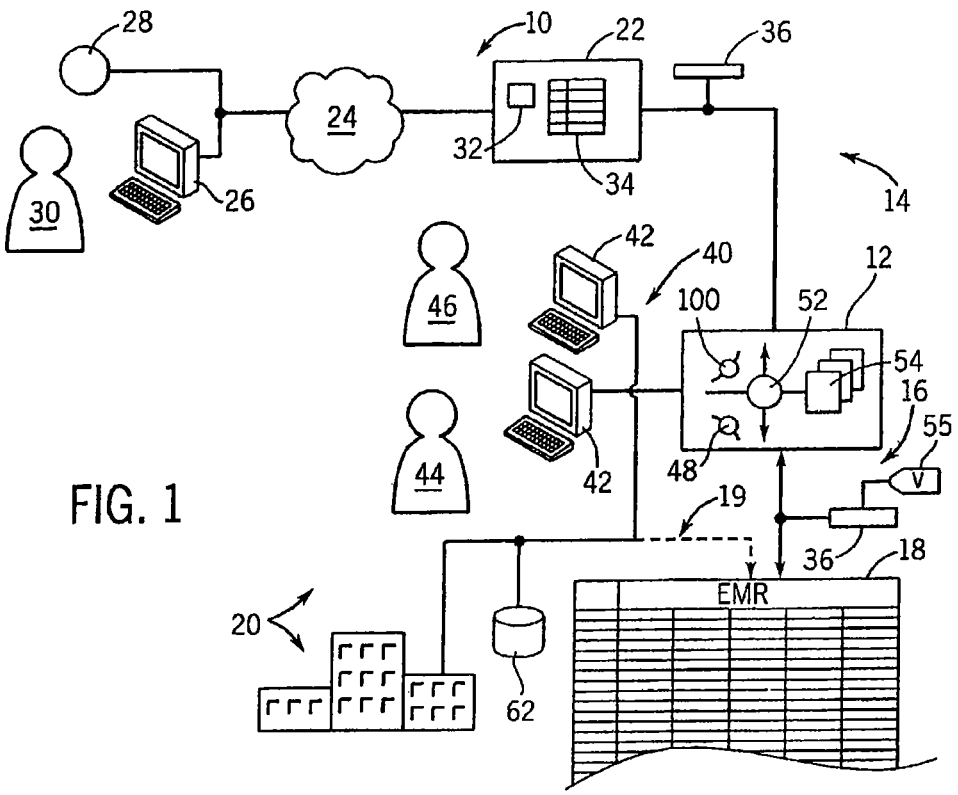
FIG. 1 is a simplified block diagram of an access program for an EMR providing an Internet communication channel.

Before the embodiments of the invention are explained in detail, it is to be understood that the invention is not limited in its application to the details of construction and the arrangement of the components set forth in the following description or illustrated in the drawings. The invention is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION OF THE PREFERRED EMBODIMENT

Referring now to FIG. 1, a computerized access system 10 per the present invention may include an interface module 12 standing between a patient communication channel 14 and an EMR communication channel 16, the latter communicating with an electronic medical record (EMR) database 18. Generally the interface module 12 is a program that may be physically located on an independent computer or run on a computer shared with another function such as the EMR database 18.

Generally, the EMR database 18 includes a complete medical history of many patients collected from a variety of healthcare sources 20 including physicians and other healthcare professionals such members of the staff at hospitals, clinics, and laboratories communicating on standard EMR network 19. As will be understood to those of ordinary skill in the art, the EMR database 18 includes biographical information about the patient describing the patient, including but not limited to the patient's age, gender, height and weight, and medical history information including the patient's medical conditions, previous medical procedures, medications, and laboratory test results. The EMR database 18 may be centrally accessed by many different healthcare sources 20 and thus serves as a path of intercommunication among many individuals working together to deliver healthcare.

The EMR database 18 is depicted as a single logical flat file for simplicity but may be configured in any of a variety of well known database formats including relational database structure, object database structures and the like. The data of the EMR database 18, like all medical records, is protected under federal law to ensure that sensitive data of this record is not released in a way that would violate a patient's privacy rights. EMR databases may be obtained from a variety of commercial sources including Epic Systems Corporation, the assignee of the present invention, which sells an EMR database under the trade name of "Chronicles" used with the "EpicCare" and "Epicenter" electronic medical record software.

The patient communication channel 14 may join the interface module 12 to a web server 22 providing a secure socket layer connection to the Internet 24. The Internet 24 may in turn connect a number of patient terminals 26 (only one shown for clarity) implementing a browser and/or a communication port to a home monitoring system 28, either or both used by a patient 30.

The monitoring system 28 may be any of a number of different healthcare appliances, for example, a blood glucose monitor or a home dialysis system or other automated home healthcare providing a machine that can support Internet or other electronic data communication. Generally, the connection to the Internet 24 allows a means for the patient 30 to enter patient-sourced medical data into the computerized access system 10, the patient-sourced medical data being either machine-generated data from home monitoring system 28 or patient-collected data manually input by a patient into terminal 26. Patient sourced data will typically include without limitation selections from: patient's weight, blood glucose, blood pressure, pain level, previous health conditions, heart rate, temperature, last menstrual period, medications, and dialysis status.

The web server 22 includes a number of active web pages 32, some of which will be described below, allowing the patient and/or monitoring system 28 to transmit and receive data securely to and from the web server 22. Incorporated into these web pages 32, for example as a CGI script, is a program for authentication of the patient's access to the web pages 32. The authentication control program makes use of a log-in identifier/password validation table 34 both shown as logically held on the web server 22 but in the preferred embodiment stored and executed remotely. The login identifier/password validation table 34 holds one or more patient specific tokens (for example, log-in identifiers and passwords but possibly including instead or in addition biometric data and the like) that ensure access to possibly sensitive medical data is not freely available to unknown parties. The patient 30 may also allow access to his or her medical records by a proxy or patient's representative also stored as links in the log-in password/password validation table 34 which gives each proxy a unique token. Generally, the term "patient" as used herein should be considered to include the patient and/or the patient's proxies. One important proxy, of a parent for children, may be initiated as a reminder based on knowledge about childbirth from the EMR.

The patient 30 must enter the login identifier and password upon every new Internet communication session. The log-in identifier and password are not stored in cookie form on the patient terminal 26 such as might make anyone with access to the patient terminal 26 able to view or enter data on behalf of the patient 30. The monitoring system 28, however, may include a different internally encoded login identifier unique to that monitoring system 28 for the same purpose.

The table 34 may also include provisions allowing several different login identifiers and passwords to be associated with the same patient so that proxy access may be had by a patient's representative.

Data received by the web server 22 from the patient 30 is marked with a patient identification number and forwarded along the patient communication channel 14 as a patient identified message 36 possibly containing a request or patient sourced data to the interface module 12. Similar messages 36 may be received by the web server 22 along the patient communication channel 14 from the interface module and forwarded to the patient 30. Generally the messages 36 will be formatted to act as queries or responses to queries of or from the EMR database 18.

Referring still to FIG. 1, the interface module 12 may also connect to a provider communication channel 40 possibly using all or a portion of standard EMR network 19 allowing communication with healthcare sources 20 via terminals 42 associated, for example, with a primary care physician 44 and a system administrator 46. The physician 44 or administrator 46 may have access to the EMR database 18 directly per normal conventions to add, modify, read, or delete data, or through the interface module 12 as will be described using a viewer/editor 48.

Access through the interface module 12 by the physician 44 also provides limited access to the patient 30. In this respect, some patient-sourced data in messages 36 sent by the patient 30 can be routed to a physician 44 and messages from the physician 44 may be routed to the patient 30 in the form of secure communications. Such secure communications may also be initiated by the patient 30 as will be described further below.

Figure 2:
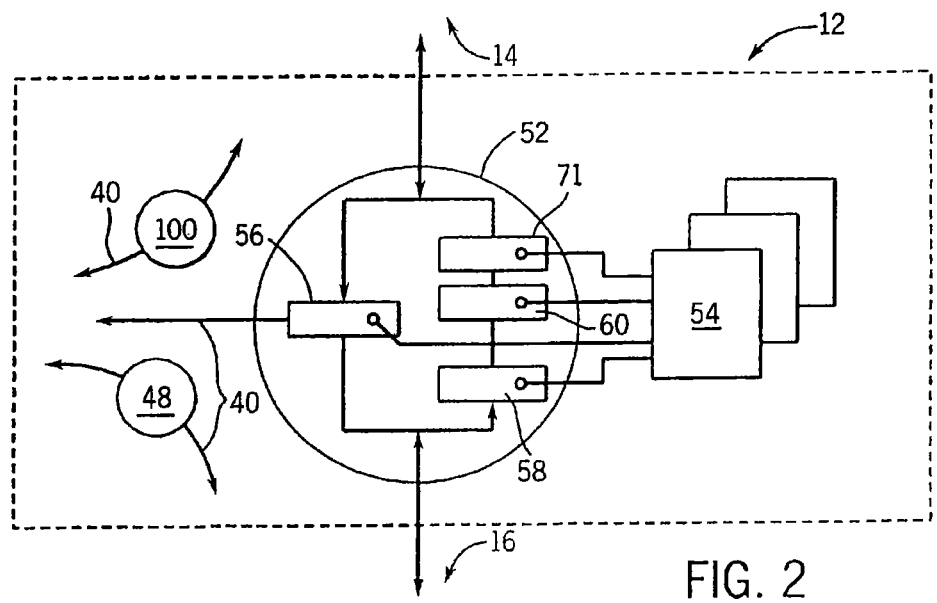
FIG. 2 is a detailed block diagram of the access program of FIG. 1 showing filters and routers moderating information flow according to user programmable rules.

Referring now to FIGS. 1 and 2, the interface module 12 employs a set of administrator programmable rules 54 to control the flow of data between the patient 30 and the EMR database 18 principally through rule engine 52. The administrator programmable rules 54 may be entered, modified, or deleted by the system administrator 46 for particular circumstances using a conventional editor program of a type well known in the art. Generally the rules are simple logical constructions describing test conditions and actions based on those test conditions as will be understood from the following discussion. The administrator in this case is considered to be an authorized individual other than the patient associated with a healthcare organization.

Generally, rule engine 52 includes a data entry filter 56 receiving data from the patient communication channel 14 and passing it to the EMR communication channel 16 and data reply filter 58 and translation program 60 and report generator 71 receiving data from the EMR communication channel 16 and passing it to the patient communication channel 14. Each of these filters and tables 56, 58, 60, and 71 applies administrator programmable rules 54 by accepting as rule arguments, the particular patient identified in a message 36 and one or more fields of the EMR database 18 being accessed for reading or writing and/or the data of those fields. User generated rules 54 can thus limit, modify or augment the data contained in messages 36 according to the type and value of data in the messages 36 and according to related data in the EMR database 18. In one example, the administrator programmable rules 54 provide the patient 30 with a controlled environment in which to view or modify records or the EMR database 18. In another example, data provided to the patient 30 may be subject to sophisticated processing, for example, trend analysis based on other data in the EMR database 18.

Figure 3:
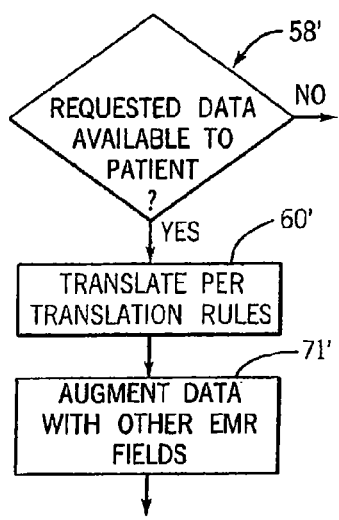
FIG. 3 is a flow chart showing the steps of data flow from the EMR to the patient.

Referring specifically to FIGS. 2 and 3, the data reply filter 58 reviews data from the EMR database 18 in response to a message 36 carrying information from the EMR database 18. At this step indicated by process block 58', the data reply filter 58 invested with administrator programmable rules 54 determines whether the requested data is to be available to the patient (or proxy-user) based on the data field or the data values themselves. The administrator programmable rules 54 may partition data of the EMR database 18 into data that may be viewed or not viewed by the patient 30. For example, nursing or progress notes may be blocked from being viewed by the patient generally regardless of their content. Alternatively or in addition, some fields of the EMR database 18 may be blocked depending on the content of the field. For example, the patient may be prohibited from viewing particular diagnoses or may have general ability to view lab tests except if the results of the test indicate that in-person consultation is to be preferred, for example, if a lab tests indicates an abnormal pap smear or HIV test. Certain data may be blocked simply to avoid clutter in the report (e.g., dates outside a certain date range) or to avoid needless distress to the patient (e.g., the patient may not wish to see they had breast cancer every time they review their problem list). The particular fields and values are determined flexible by the user programmable rules 54 and may be changed on a patient-by-patient basis. Further, data may be made generally available to patients, but an option may be given to the provider to block the data from patient access.

If permission is granted for the data to be received by the patient 30, the response message 36 containing the data proceeds to a translation program 60 which provides a set of patient-friendly words and phrases that may be substituted for words and phrases within the response message 36 to improve the intelligibility of the reply message to a layperson. The rules in this case simply effect a search and replace operation of a type well understood in the art as indicated by process block 60'. For example, a medical term such as "esophageal reflux" might be translated to "chronic heartburn" for a lay user by means of a series of search and replace type operations in the rules 54 or by selecting a different interpretation text for standard medical codes.

Data from the translation program 60 may be received by the report generator 71 which calls on other data from the EMR database 18 to augment the requested data of the message 36 or to put the requested data in context as indicated by process block 71'. For example, the report generator may prepare a chart comparing requested test results for the patient 30 to an ideal range based on patient-sourced data held in the EMR database 18 such as patient age, gender or other medical conditions. Alternatively, the report generator 71 may provide previously stored data to produce a time series putting the data in context. The report generator 71 may also provide the patient 30 with general patient information keyed to or tailored to the patient 30 based on the patient records, for example, general patient information about exercise geared to the patient's age or diet. This general patient information may be contained in a non-patient record file 62 as shown in FIG. 1 and provided by a third party vendor. This general patient information can also be triggered by the trend checker 66 which may help identify possible medical issues. The general patient information can include preprepared background information about the medical issue and clinical options for treatment.

Importantly, the report generator 71 may make use of data from the EMR database 18 not directly available to the patient. For example, a patient may be blocked from certain data related to the patient's mental health, but this information can be used to provide the patient with relevant content from the non-patient record file 62 including articles on dealing with stress or about counseling services. The report generator 71 may produce reminders, for example, for a pap smear, based on hidden data about sexual history. A report, for example, may show data about weight gain and cholesterol levels to encourage progress on these fronts, while hiding a diagnosis about obesity which might make the patient feel defeated.

Figure 4:
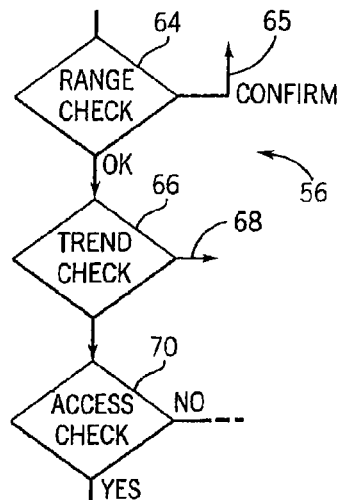
FIG. 4 is a flow chart similar to that of FIG. 3 showing the steps of data from the patient to the EMR.

Referring again to FIGS. 2 and 4, patient medical data coming from the patient 30 (patient-sourced data) is received by data entry filter 56 where it is first processed to determine that the patient-sourced data provided by the patient 30 objectively matches the particular range expected from that data per process block 64. Such patient-sourced data may include, for example, a patient's weight, blood glucose, blood pressure, and dialysis information for a dialysis machine. For example, a blood pressure entry by the patient may be checked against theoretically possible blood pressure entry values. If the value entered by the patient 30 does not fit within an expected range, a "request to confirm" message is sent as indicated by arrow 65. In response, the patient 30 may check and reenter that data. Alternatively, or in addition the range checking may flag the data for review by the physician 44 later who is also provided with a direct link to the data so that it may be easily examined and/or corrected. The patient-sourced data may be entered in response to a reminder message sent to the patient according to a stored reminder program as part of the computerized access system 10.

The range checking process block 64 may also request and receive from data in the EMR database 18, for example, data indicating recent similar data provided by the patient 30 to which the current data may be compared, or known medications taken by the patient 30 that might modify the range. Thus, the range checking may be invested with knowledge about the patient from the EMR database 18 including data that is not directly accessible to the patient.

If the patient 30 confirms the patient-sourced data or if the patient-sourced data passes the range checker 64, a data trend is checked per process block 66 which evaluates the data in light of other known data in the EMR database 18, for example, previous entries of data by the patient 30 and known medical conditions of the patient 30. Typically, trend checking will evaluate given patient-sourced data by extrapolating from previous data or other data in the EMR database 18. If the trend or simply an abnormal individual reading indicates a problem such as might require review by a healthcare professional, a message indicated by arrow 68 is provided to a physician 44 alerting them as to this trend which the healthcare professional might otherwise have noticed only by entering the data his or herself. The patient may be notified to seek an appointment and may be connected to a scheduling system or office.

Abnormal conditions detected by the trend checker can in addition notify the patient to call an emergency number or a provider on-call for immediate response, for example, significant change in blood pressure or heart rate as informed by data in the EMR database 18. Importantly, the trend checking can be informed by information about the patient obtained from the EMR database 18 as described by a rule 54. For example, a patient who has had congestive heart failure might be subject to a trend rule that is sensitive to a lower level of weight gain than is a person without such a condition. Likewise, a different trend rule might be used for a patient who has taken a medication (as indicated in the EMR database 18) that sometimes raises blood pressure or where a slight blood pressure rise signals a possible problem associated with the drug.

After the patient-sourced data has passed through the trend checking, process block 70 confirms that the patient-sourced data may be entered into the patient record of the EMR database 18. This access checker 70 is a logical construct and in fact normally implemented by activation of one or more web pages 32 allowing for particular data entry by the patient. A significant amount of the data of the EMR database 18 accessible to the patient will be read-only and in general, only a small subset of data will allow for data entry by the patient 30.

Figure 7:
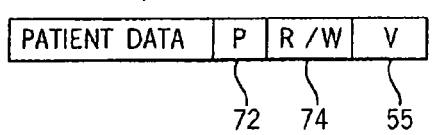
FIG. 7 is a logical diagram of patient-sourced data entered into the electronic medical record showing additional fields used for validation and control.

Referring now to FIG. 7, all patient-sourced data of message 36 entered into the EMR database 18 carries with it a patient-source tag 72 indicating that it is patient originated data. This patient-source tag 72 is always kept with the patient-sourced data to preserve the integrity of the EMR database 18. Nevertheless, the patient-sourced data is available freely to other users of the EMR database 18 to integrate the patient-sourced data with the healthcare system. The patient-sourced data of message 36 may also include a second read/write field 74 indicating whether the patient may continue to edit the data or whether it has become read-only data with respect to the patient. This read/write field may be carried with the data or may be enrolled in an administrator programmable rule 54 of the rule engine 52 and prevents delayed modification of data by the patient preserving data integrity. Normally data that may be written to (or modified) by the patient 30 is converted to read-only status after a predetermined period of time selected by an administrator 46. Finally, the patient-sourced data of message 36 may also include a validation tag 55 which may be provided optionally for data that has been validated by a healthcare professional indicating that it has additional reliability. This validation tag 55 may be attached by the physician 44 or administrator 46 using the viewer/editor 48 to review data from the patient after it has been enrolled in the EMR database 18 or as prompted by a message generated by rule engine 52. Importantly, the physician 44 does not need to recopy or re-enter the data, but may simply validate existing data.

Data within the EMR database 18 can be viewed in a number of ways based on these tags. Only validated data can be viewed or only invalidated, patient-sourced data may be viewed. Alternatively both types of data may be commingled with or without the tags being identified. In a third display method, the screen can be separated into a field reserved for each type of tagged data.

The patient-sourced data may be formatted by the web server 22 or the interface module to properly query the EMR database 18, in this case query referring both to operations of a standard query language including those that read, write, sort and search for data.

Figure 5:
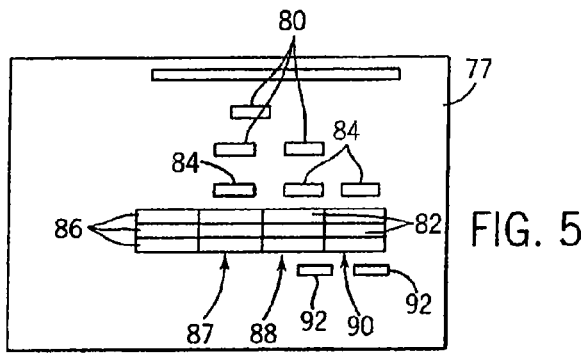
FIG. 5 is an example screen of an Internet browser displayed to the patient of FIG. 1 for the entry and editing of data.

Referring now to FIGS. 1 and 5, the entry of patient-sourced data by the patient 30 or the request and review of data from the EMR database 18 is facilitated by a data entry screen 77 generated by the browser on the patient terminal 26 from data provided by the web server 22. The data entry screen 77, for example, may provide data entry boxes 80 allowing the patient to designate data fields from the EMR database 18 for review or data for entry into particular fields of the EMR database 18 and data display fields 82 in which data from the EMR database 18 may be displayed. Data collected over a period of time may be indicated in tabular form with rows 86 being data types and columns being dates and times of the data per date flags 84 so that a first column 87 may allow for current data entry by the patient whereas later columns 88 and 90 may show previously entered data by the patient. An edit flag 92 may indicate whether the data is still editable by the patient (per read/write field 74) or whether it has reverted to a read only status. Triggers other than time, such as validation of the data or its range can be used in addition to or instead based on programmable rules.

Figure 6:
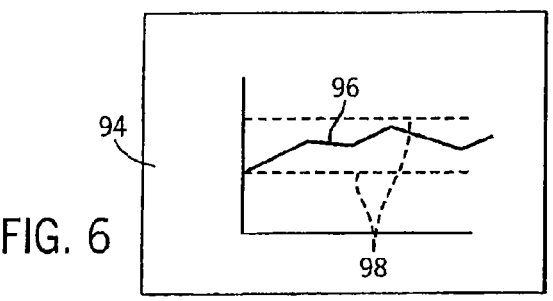
FIG. 6 is a screen similar to that of FIG. 5 showing an example representation of data provided to the patient.

Alternatively, data may be reviewed on a data review screen 94 as shown in FIG. 6. In this data review screen 94 shows a line plot 96 of previous data obtained from the EMR database 18 and normal bars 98 based on knowledge about the patient obtained from the patients EMR database 18. The patient, for example, may also view other aspects of the EMR database 18. For example, a history of prescriptions and their status or the results of previous office visits which may also be viewed by a proxy for example, a parent or guardian.

Referring again to FIG. 2, the present invention, providing communication with the patient 30 over the Internet 24, allows for secure communication between the patient 30 and physician 44 via a dedicated messaging server 100 contained within the interface module 12. Incorporation of the messaging system into the present invention allows the physician to review messages in light of data read or viewed from the EMR communication channel 16.

It is specifically intended that the present invention not be limited to the embodiments and illustrations contained herein, but include modified forms of those embodiments including portions of the embodiments and combinations of elements of different embodiments as come within the scope of the following claims.

What is claimed is:

1. A computer-implemented electronic medical record (EMR) access control system configured to implement an access program stored on a computer-readable medium comprising:
   a computer, which when controlled by the access control program, is configured to:
   a) receive patient-sourced medical data about a patient generated and entered into the computer by the patient from the patient at a patient computer system;
   b) generate a trend analysis based on previously received patient-sourced medical data that does not include healthcare provider-sourced medical data;
   c) generate a patient specific data range based on healthcare provider-sourced medical data generated based on interaction between the patient and a healthcare provider in a computer-implemented electronic medical record system of the healthcare provider; wherein the healthcare provider-sourced medical data does not include patient-sourced medical data;
   d) compare the received patient-sourced medical data to the trend analysis and the patient specific data range and determine that the received patient-sourced medical data is not an outlier when compared to the trend analysis and is within the patient specific data range; and
   e) incorporate the received patient-sourced medical data based on the determination into a patient-sourced medical data section of the computer-implemented electronic medical record system of the healthcare provider, tagging the received data as patient-sourced medical data to generate tagged patient sourced medical data stored on the computer system,
   wherein the access program is configured to block access to the computer-implemented electronic medical record system by the patient.

2. The computer-implemented electronic medical record (EMR) access control system of claim 1, wherein comparing the received patient-sourced medical data to the trend analysis and the patient specific data range includes testing the data for entry errors based on knowledge about the patient held in the electronic medical record of the healthcare provider.

3. The computer-implemented electronic medical record (EMR) access control system of claim 2, wherein the patient is notified of the entry errors to permit re-entry of the patient-sourced medical data.

4. The computer-implemented electronic medical record (EMR) access control system of claim 1, further including, providing output to the patient indicating a medical issue based on the comparison.

5. The computer-implemented electronic medical record (EMR) access control system of claim 4, wherein the computer provides the patient with prepared background information about the medical issue.

6. The computer-implemented electronic medical record (EMR) access control system of claim 4, wherein the computer provides the patient with clinical options for assisting in correcting the medical issue.

7. The computer-implemented electronic medical record (EMR) access control system of claim 4, wherein the patient is prompted to seek healthcare support.

8. The computer-implemented electronic medical record (EMR) access control system of claim 1, wherein a healthcare professional is notified of abnormal conditions indicated by the patient-sourced data to permit review of the patient-sourced data.

9. The computer-implemented electronic medical record (EMR) access control system of claim 8, wherein the healthcare professional is notified by a secure electronic message.

10. The computer-implemented electronic medical record (EMR) access control system of claim 1, wherein the patient-sourced data is selected from the group consisting of: patient's weight, blood glucose, blood pressure, pain level, previous health conditions, heart rate, temperature, last menstrual period, and dialysis status.

11. The computer-implemented electronic medical record (EMR) access control system of claim 1, wherein the patient-sourced data from the patient is authenticated by a patient specific token.

12. The computer-implemented electronic medical record (EMR) access control system of claim 1, wherein the electronic medical record of the healthcare provider holds medical data provided by different healthcare professionals for multiple patients.

13. The computer-implemented electronic medical record (EMR) access control system of claim 1, wherein the access control program includes a web server and the patient-sourced data is received over the Internet from a web browser.

14. The computer-implemented electronic medical record (EMR) access control system of claim 1, wherein the patient-sourced data is further presented to a healthcare professional for validation prior to being entered into the electronic medical record of the healthcare provider.

15. The computer-implemented electronic medical record (EMR) access control system of claim 1, wherein patient-sourced data is selected from a source consisting of: machine-generated data from home, healthcare appliances and patient-collected data manually input by a patient.

16. A computer-implemented method stored on a computer-readable medium for implementing an electronic medical record (EMR) access program, comprising the steps of:
   a) receiving patient-sourced medical data about a patient generated and entered into the computer by the patient from the patient at a patient computer system;
   b) generate a trend analysis based on previously received patient-sourced medical data that does not include healthcare provider-sourced medical data;

c) generate a patient specific data range based on healthcare provider-sourced medical data generated based on interaction between the patient and a healthcare provider in a computer-implemented electronic medical record system of the healthcare provider; wherein the healthcare provider-sourced medical data does not include patient-sourced medical data;

d) compare the received patient-sourced medical data to the trend analysis and the patient specific data range and determine that the received patient-sourced medical data is not an outlier when compared to the trend analysis and is within the patient specific data range; and e) incorporate the received patient-sourced medical data based on the determination into a patient-sourced medical data section of the computer-implemented electronic medical record system of the healthcare provider, tagging the received data as patient-sourced medical data to generate tagged patient sourced medical data stored on the computer system, wherein the access program is configured to block access to the computer-implemented electronic medical record system by the patient.

17. The computer-implemented method of claim 16, wherein comparing the received patient-sourced medical data to the trend analysis and the patient specific data range includes testing the data for entry errors based on knowledge about the patient held in the electronic medical record of the healthcare provider.

18. The computer-implemented method of claim 16, wherein a healthcare professional is notified of abnormal conditions indicated by the patient-sourced data to permit review of the patient-sourced data.

19. The computer-implemented method of claim 16, further including displaying data from the computer-implemented electronic medical record system according to a format selected from the group consisting of: simultaneously displayed but spatially segregated patient-sourced data and healthcare-provider-sourced data, healthcare-provider-sourced data only, patient-sourced data only, and commingled patient-sourced data and healthcare-provider-sourced data.

20. A computer-implemented electronic medical record (EMR) access control system configured to implement an access program stored on a computer-readable medium comprising:

a computer, which when controlled by the access control program, is configured to:

a) receive patient-sourced medical data about a patient generated and entered into the computer by the patient from the patient at a patient computer system;

b) generate a trend analysis based on previously received patient-sourced medical data that does not include healthcare provider-sourced medical data;

c) generate a patient specific data range based on healthcare provider-sourced medical data generated based on interaction between the patient and a healthcare provider in a computer-implemented electronic medical record system of a healthcare provider; wherein the healthcare provider-sourced medical data does not include patient-sourced medical data;

d) compare the received patient-sourced medical data to the trend analysis and the patient specific data range and determine that the received patient-sourced medical data is not an outlier when compared to the trend analysis and is within the patient specific data range; and e) incorporate the received patient-sourced medical data based on the determination into a patient-sourced medical data section of the computer-implemented electronic medical record system of the healthcare provider, tagging the received data as patient-sourced medical data to generate tagged patient sourced medical data stored on the computer system.

\* \* \* \* \*